United States Patent [19]

Gross et al.

[11] Patent Number: 5,227,720
[45] Date of Patent: Jul. 13, 1993

[54] APPARATUS AND METHOD USING A BIFILAR COIL WITH AN INTEGRATED LOOP/SWITCH FOR RESISTANCE MEASUREMENT OF SUPERCONDUCTORS

[75] Inventors: Dan A. Gross; Mark E. Vermilyea, both of Niskayuna, N.Y.

[73] Assignee: General Electric Company, Schenectady, N.Y.

[21] Appl. No.: 862,148

[22] Filed: Apr. 2, 1992

[51] Int. Cl.[5] .................... G01R 33/12; G01R 27/00; G01N 27/04; G01N 27/72
[52] U.S. Cl. ................................ 324/235; 324/224; 324/263; 324/691; 505/843
[58] Field of Search ............... 324/224, 228, 235, 262, 324/263, 691; 505/843

[56] References Cited

U.S. PATENT DOCUMENTS

| | | | |
|---|---|---|---|
| 3,359,495 | 12/1967 | McMaster et al. | 324/235 |
| 3,449,664 | 6/1969 | Smith | 324/235 |
| 5,140,266 | 8/1992 | Dorri et al. | 324/228 |

*Primary Examiner*—Gerard R. Strecker
*Attorney, Agent, or Firm*—James R. McDaniel; Paul R. Webb, II

[57] ABSTRACT

This invention relates to an apparatus and method for measuring the resistance of superconductors. Structures of this type, generally, allow the resistance of the superconductor to be accurately measured in a non-destructive manner by using a bifilar coil which includes an integrated loop/switch formed from the bifilar coil.

12 Claims, 5 Drawing Sheets

APPARATUS AND METHOD USING A BIFILAR COIL WITH AN INTEGRATED LOOP/SWITCH FOR RESISTANCE MEASUREMENT OF SUPERCONDUCTORS

BACKGROUND OF THE INVENTION

1. Field of the Invention

This invention relates to an apparatus and method for measuring the resistance of superconductors. Structures of this type, generally, allow the resistance of the superconductor to be accurately measured in a non-destructive manner by using a bifilar coil which includes an integrated loop/switch formed from the bifilar coil.

2. Description of the Related Art

The use of superconductors for production devices has a problem in that the resistance (or absence thereof) of a long length of material cannot be easily measured nondestructively, i.e. without actually building the device and measuring its field accurately over time. The reason for this is that in producing the desired field, the current in the conductor also produces large forces on the conductor which require the conductor to be potted in a hard material, such as epoxy to avoid motion and consequent quenching of the superconductor.

One way to address this issue is to wind a bifilar coil, wherein two conductors are wound adjacent to one another so that current will flow in opposite directions when the winding is excited. The field thus produced is very low and the coil can typically be wound "dry" without concern about the forces, the resultant motion and quenching. This facilitates unwinding after a successful test and subsequent rewinding into the desired field-producing coil configuration. The bifilar coil can then be excited from its end leads and the voltage across the leads measured at a given current to infer the resistance of the conductor.

The measurement which is desired from such a screening test is one of the overall resistance of the length of superconductor together with any joints which may be present in it. Unfortunately, the resistance which is required for a persistent current device such as an MR magnet is very low, and therefore difficult to detect by voltage measurements. An estimate of the resistance level which must be attained for a given device can be made from an equation governing the behavior of a circuit with a series resistance (R) and inductance (L) (FIG. 1). For a given initial current $I_o$ at time 0, the current at time t is given by $$I = I_o e^{-tR/L} \qquad (Eq. 1).$$

For example, the specification for field drift rate for an MR magnet is typically 0.1 ppm/hr. Solving Equation 1 for R/L with this desired current drift rate (the current and field are linearly related) yields $R/L = 2.8e^{-11}$ $\Omega/H$. For a magnet with an inductance of 20 Henries, the overall coil resistance must be no greater than $5.6e^{-10} \Omega$. At a current of 150 A, the voltage generated by such a resistance is $83e^{-9}$ V. Because of thermally induced voltages in the sensing leads and at junctions, as well as, other effects, the accurate measurement of such a low voltage is very difficult—a typical limitation on accurate voltage measurement is perhaps $100e^{-9}$ V. Therefore, inference of resistance of the sample of superconductor from the measured voltage can lead to results which are not of the required accuracy.

Resistance tests of superconductors have been made in the past by measuring the voltage at a given current for long (up to 70,000 feet) and short (4–12 inches) lengths of conductor. Resistance has been measured from drift tests on individual loops of conductor, but this qualifies only that short length of material and is not useful for qualifying lengths which are required to wind a complete magnet. Therefore, a more advantageous system, then would be presented if the resistance of long lengths of superconductor could be measured in a non-destructive manner.

It is apparent from the above that there exists a need in the art for a system which measures the resistance of a superconductor, and which at least equals the voltage measurement accuracy of the known measurement systems, but which at the same time is capable of measuring long lengths of superconductor. It is a purpose of this invention to fulfill this and other needs in the art in a manner more apparent to the skilled artisan once given the following disclosure.

SUMMARY OF THE INVENTION

Generally speaking, this invention fulfills these needs by providing an apparatus for measuring the resistance of a superconductor, comprising a bifilar coil having a loop formed substantially integrally with said coil and a field measuring means located substantially adjacent to said loop.

In certain preferred embodiments, the bifilar coil is wound with paired conductors which carry current in opposite directions to minimize the field, and the forces created in the coil. The coil includes a loop which is formed from the radially outboard of the two paired conductors in the last (outboard) layer. The loop performs two functions with a heater attached. The loop acts as a switch to allow the bifilar coil to be ramped up to a desired current level, and the loop also acts as a field generator which can be used to infer the current in the conductor. The drift rate of the current, coupled with the known (calculated or measured) inductance of the bifilar coil, allows an accurate computation of the overall resistance of the coil and any joints therein.

A direct extension of the proposed concept performs the resistance measurement in a background magnetic field. The advantage of this method is that it allows exploration of the resistance of the tested conductor in the actual operating regime which it will see the when the conductor is wound into a magnet. This magnetic field may be imposed on the coil by a solenoidal or other suitable winding which is powered by a highly stable power supply, or which is separately rendered persistent with a superconducting switch. Background magnetic field effects on the desired field measurement are minimized by ensuring that the background field is orthogonal to the field of the loop and by using field measurement techniques which integrate the field around a loop which contains no part of the field coil.

In another further preferred embodiment, the resistance of the superconductor can be accurately measured in a non-destructive manner.

The preferred superconductor measurement system, according to this invention, offers the following advantages: ease of use; excellent resistance measurements characteristics; excellent economy; good stability; and high strength for safety. In fact, in many of the preferred embodiments, these factors of use, resistance measurement characteristics, and economy are optimized to an extent that is considerably higher than heretofore achieved in prior, known superconductor measurement systems.

BRIEF DESCRIPTION OF THE INVENTION

The above and other features of the present invention which will become more apparent as the description proceeds are best understood by considering the following detailed description in conjunction with the accompanying drawings wherein like characters represent like parts throughout the several views and in which.

DETAILED DESCRIPTION OF THE INVENTION

Figure 1:
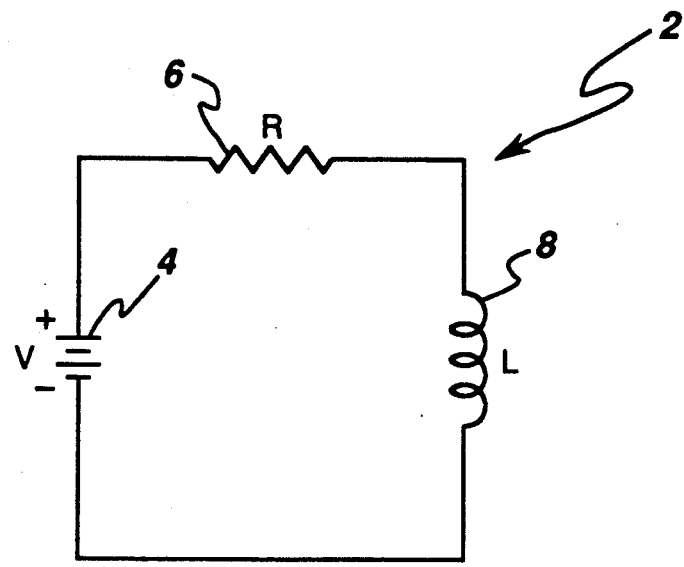
FIG. 1 is a R-L circuit diagram for a superconducting coil, according to the prior art.

As discussed earlier, FIG. 1 is a prior art diagram for a R-L circuit 2 for a conventional superconducting coil. Circuit 2 includes power source (V) 4, resistor (R) 6 and inductor (L) 8.

As disclosed by the present invention, a more accurate measurement of the resistance of a length of conductor than is obtainable from voltage measurements can be obtained by connecting the conductor with superconducting joints in a closed loop circuit, inducing a current into it, and reading the field created by its current over a long time. Since the field varies linearly with the current, this amounts to measuring the current drift. The resistance of a length of conductor with an inductance L over a time interval $\Delta t$ is given by $$R = (0.05)L/\Delta t \quad \text{(Eq. 2)}.$$

A reasonable time interval over which to measure the field is one day, or 86,400 s. A bifilar coil typically wound of 70,000 feet of tape superconductor (enough to make a 0.5T MR magnet) has an inductance of about 1200 μH. This value is independent of the diameter and length of the coil, as it involves only the spacing between and the length of the two conductors. It may be derived as the inductance of a pair of parallel conductors carrying oppositely directed currents from Gauss' Law in the form:

$$\lambda = \frac{\mu_o g}{2w} \quad \text{(Eq. 3)}$$

where $\lambda$ is the inductance in Henries/meter, g and w are the gap between and width of the conductors, respectively, and $\mu_o$ is the magnetic permeability of free space. Alternatively, the inductance may be experimentally derived from measurement of the voltage required to create a given rate of current change in the coil. Such a measurement should be carried out over a region of no appreciable flux penetration into the superconductor, or preferably in the normal state but at low temperature so the resistive effects are minimized. Using the 1200 μH calculated value of inductance, from Eq. 3, the resistance from Eq. 2 corresponding to a 4% field drop over one day is $5.6e - 10\Omega$. This is equal to the resistance value which must be measured. The 4% field measurement accuracy is well within the range of a Hall sensor.

Figure 2:
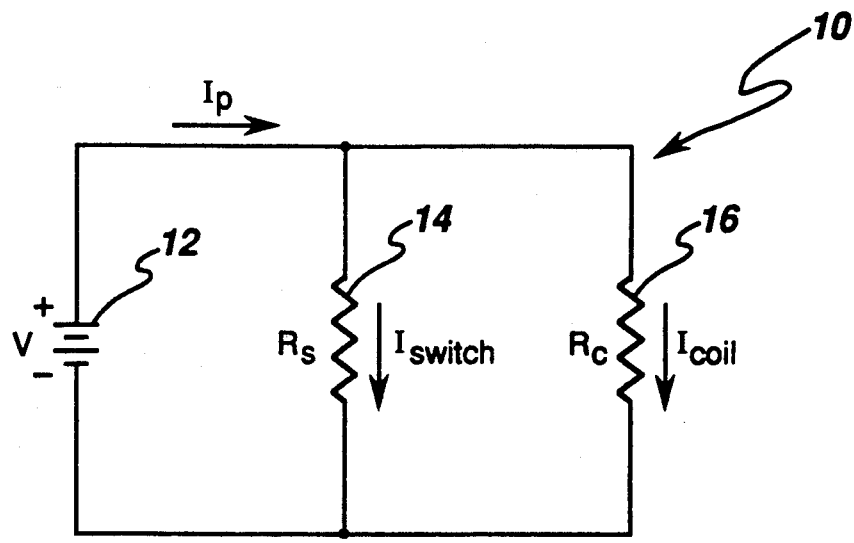
FIG. 2 is a circuit diagram for the switch/coil, according to the present invention.

This preferred test can be accomplished with a superconductor by attaching the current leads to form a parallel circuit having as one leg a short length of conductor (called a switch) which may be driven above its transition temperature with a small heater and as the other the bulk of the coil (see FIG. 2). In particular, FIG. 2 illustrates circuit 10 including power source 12, switch resistor 14 and coil resistor 16.

Figure 3:
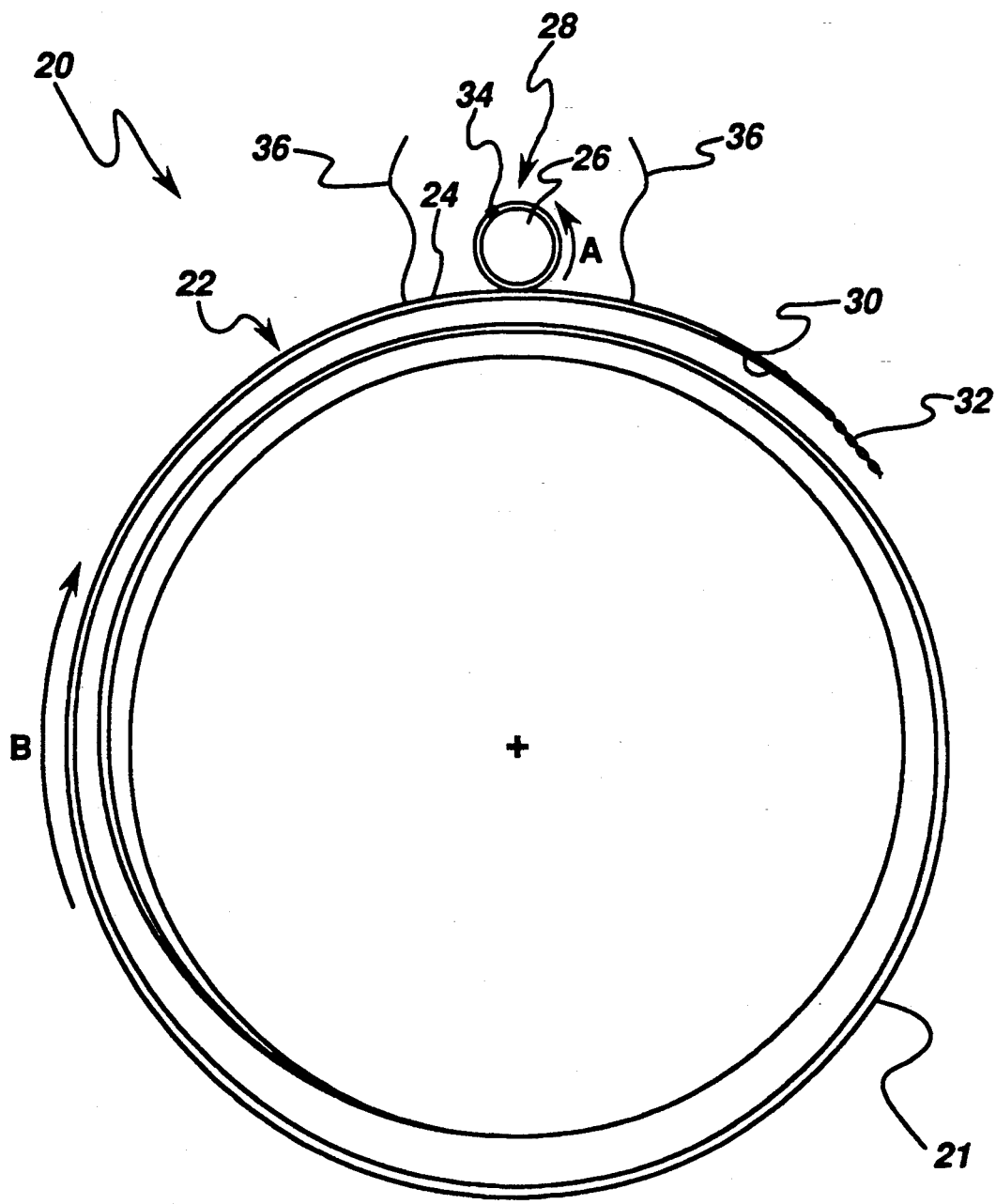
FIG. 3 is a schematic illustration of the loop/switch for a bifilar winding, according to the present invention.

With respect to FIG. 3, the simplest embodiment of switch assembly 20 is formed by wrapping along the direction of arrow A a portion of the radially outermost turn of one conductor 24 of the paired bifilar conductors 22 around a mandrel 26 of the desired diameter in the opposite direction to that of the plural turn coil winding 21 formed by said bifilar conductors which is being wrapped in the direction of arrow B for a single turn to form switch 28 on mandrel 26 before it rejoins the radially outermost turn of the other conductor 30 to complete the final turn of the bifilar coil with a pigtail-type joint 32. In order to induce the desired current in coil winding 21, switch 28 is turned normal by powering a conventional heater 34 attached to switch 28 by conventional fasteners, energizing power leads 36, and allowing the current to stabilize. The currents flowing in the coil ($I_c$) and the switch ($I_s$) are determined from the resistances of the two sides of the circuit and the power supply current $I_p$ by the equations $$\frac{I_c}{I_s} = \frac{R_s}{R_c} \text{ and } I_c + I_s = I_p \quad \text{(Eq. 4)}$$

which can be rearranged as $$\frac{I_s}{I_p} = \frac{R_c}{R_s + R_c} \text{ and } \frac{I_c}{I_p} = \frac{R_s}{R_s + R_c} \quad \text{(Eq. 5)}$$

The switch resistance which can be generated by heating a length of tape superconductor is governed by the resistivity of the copper stabilizer in the tape, which has a resistivity ratio of about 75 which indicates a low temperature (4-20K) resistivity of about $2.27e - 8\Omega/cm$. The copper, preferably, is 0.015 cm thick and 0.3 cm wide, so the resistance per unit length is $5\mu\Omega/cm$. Therefore, a conventional 1 inch heater will produce a resistance of about $13\mu\Omega$. Note that the tape temperature is below the transition temperature very close to the boundary of the heater because of the excellent thermal conductivity of the copper in the tape, so the length of the normal region in the switch is essentially equal to the length of the heater. Since the coil resistance is unknown, the fraction of the current which circulates in the coil will also be unknown. However, a desirable coil resistance is in the $n\Omega$ range. Using 13 $n\Omega$ as a working value, the coil current will be $0.999I_p$. Should the resistance of the coil be significantly higher then $13n\Omega$, it will not affect the ability of the apparatus to yield an accurate resistance measurement. This is determined solely from field drift rate and inductance. But the current at which the resistance is measured will be a smaller fraction of the power supply current. Even at a coil resistance of 1.3 $\mu\Omega$, the coil current will still be about $0.911 I_p$. This is not seen as a significant drawback to this testing method.

The placement of the field sensor is an important part of the proposed testing technique, because there are fields generated by means other than the transport current in the superconductor. These means include circulating currents which are driven by changes in magnetic flux in the region of the conductor and Meissner effect currents. Fortunately, these fields drop off as a higher power of the distance from the coil than does that produced by the transport current. In order to ensure that the effects of the fields from circulating currents are minimal, the field sensor must be placed sufficiently far from the coil that the transport current field dominates the reading. For instance, while the center of the switch loop is an attractive place to position the sensor, the field from circulating currents in the main coil at that position may be substantial. Since the bifilar coil actually produces a finite field at a distance away from the coil where the circulating current field is small, the field of the loop is not required for the measurement. In fact, a location distinct from the center of the loop is preferred.

Figure 4:
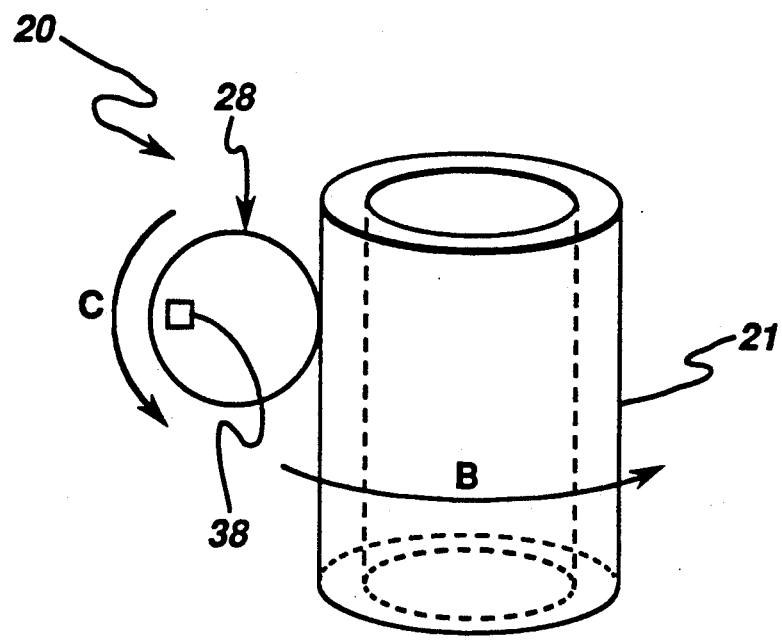
FIG. 4 is a second embodiment of the loop/switch for a bifilar winding.

Thus far the geometry has been presented in which the loop extension from the coil is in a plane perpendicular to the axis of the bifilar coil. While this is the easiest winding geometry, especially for tape conductor, it presents a difficulty because the principal fields of the bifilar coil and the loop extension are in the same direction. With respect to FIG. 4, in order to minimize the effects of the field of the bifilar coil, the loop extension or switch 28 may be aligned with its plane perpendicular to the direction of arrow C along the azimuthal (circumferential) direction (the direction of arrow B of the bifilar coil winding 21). Since the bifilar coil field has only radial and axial components, Hall sensor 38 measures only the field of the loop extension or switch 28, which is preferred. Three other preferences for the loop extension 28 location relative to the coil 21 are:

1. radially far from the coil winding 21 (provided a large radius dewar is available);
2. axially far from the coil winding 21 (provided a large height dewar is available);
3. reaching to a location which allows placement of Hall sensor 38 on the bifilar coil winding axis.

Figure 5:
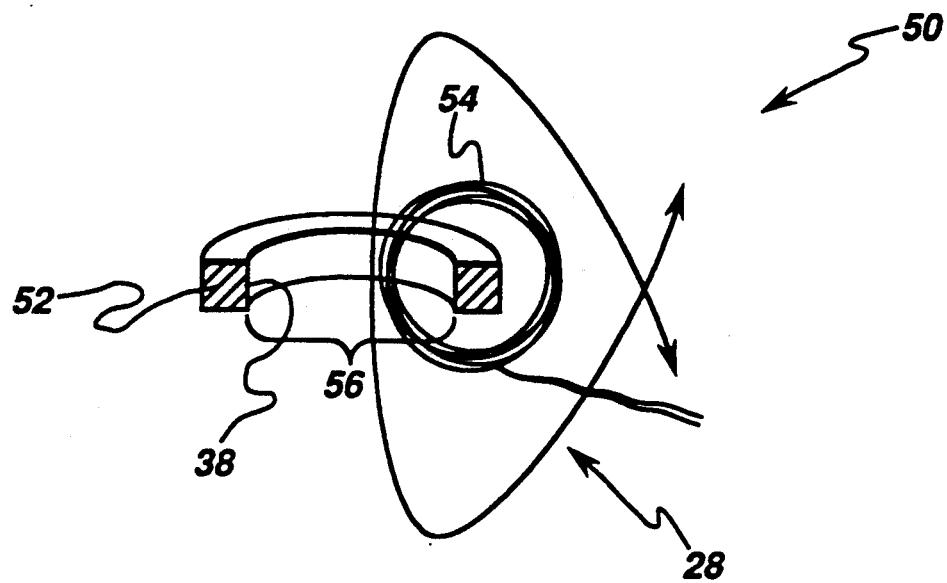
FIG. 5 is a third embodiment of the loop/switch for a bifilar winding.

With respect to FIG. 5, the measured field contributions from Meissner effect circulating currents in the tape superconductor comprising the loop extension or switch 28 can be eliminated by coupling a ring 52, preferably, made of ferrite, mild steel, or other suitable ferromagnetic material to the loop extension or switch 28. Ring 52 has a gap 56 in which a Hall sensor 38 could be placed to measure the flux circulating in the ring, without being affected by the field of the bifilar coil winding 21 or the circulating currents in the loop extension or switch 28. The current sensitivity expression for the loop extension is:

$$I = \frac{\int B \cdot dl}{\mu_o \mu_{rel}} \quad \text{(Eq. 6)}$$

where I is the transport current in the loop, dl the differential length along the iron ring, B the flux density in the ring, $\mu_{rel}$ the relative permeability of the ring, and $\mu_o$ is the magnetic permeability of free space. The calibration of ring 52 is achieved by winding a coil 54 on the ring 52 in a toroidal fashion such that any magnetic flux change in ring 52 will induce a current in the toroidal coil 54. Coil 54, preferably, is constructed of copper. Note that the toroidal or calibration coil 54 need not be a complete toroid, but may be only cover part of the circumference of the ring 52. In the linear range of a conventional B-H curve for the ferrite or soft iron ring 52, the toroidal current is linearly dependent on the current in the loop extension 28.

The same toroidal calibration coil 54 can be used to null out the field of the loop extension or switch 28 for the purpose of improving the accuracy of measuring the deviation from that null. In this configuration, the temporal stability of Hall sensor 38 can be enhanced by reducing the contribution of loop extension or switch 28 and by using a conventional highly stable calibrated current source, such as, is used in the powering Hall sensor 38 itself. A temporal stability of about 10 ppm has been achieved in this manner.

Figure 6A:
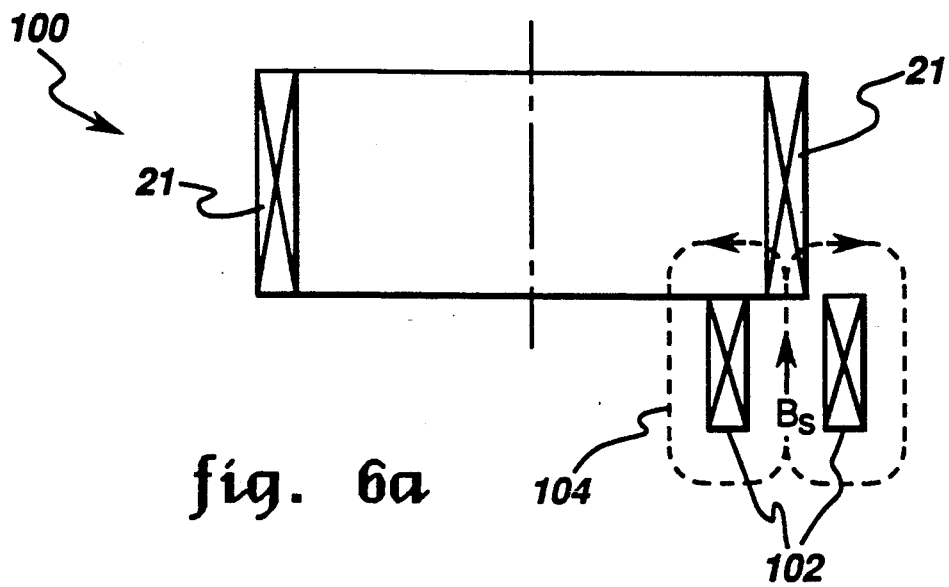
FIG. 6a is a schematic illustration of a apparatus for placing a background magnet field on a bifilar coil, according to the present invention.
Figure 6B:
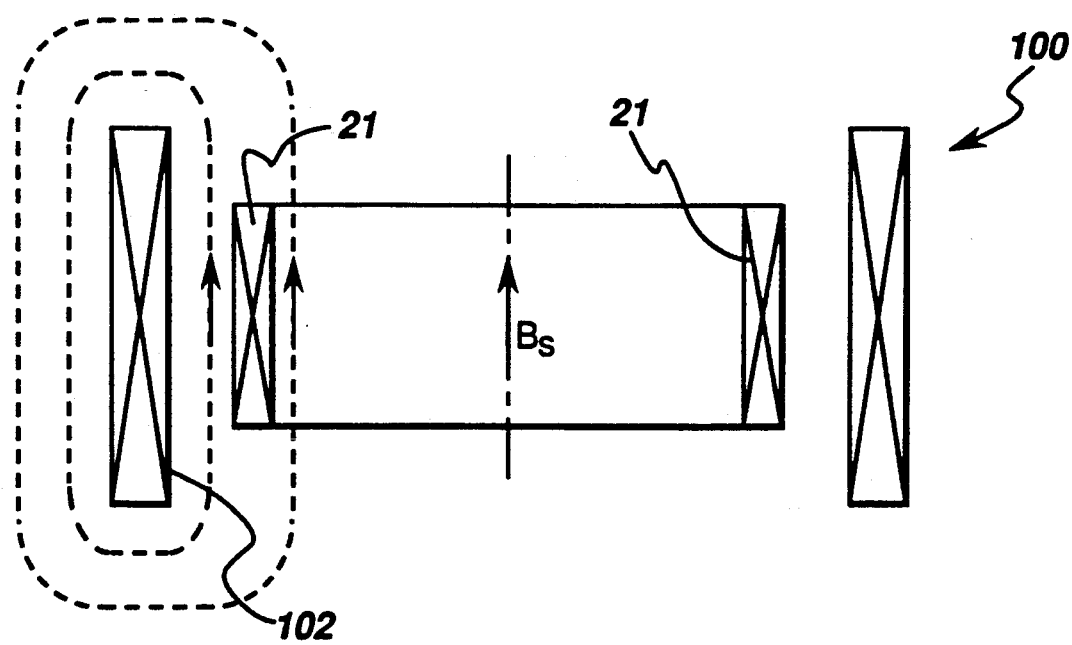
FIG. 6b is a second embodiment of an apparatus for placing a background magnetic field on a bifilar coil.
Figure 6C:
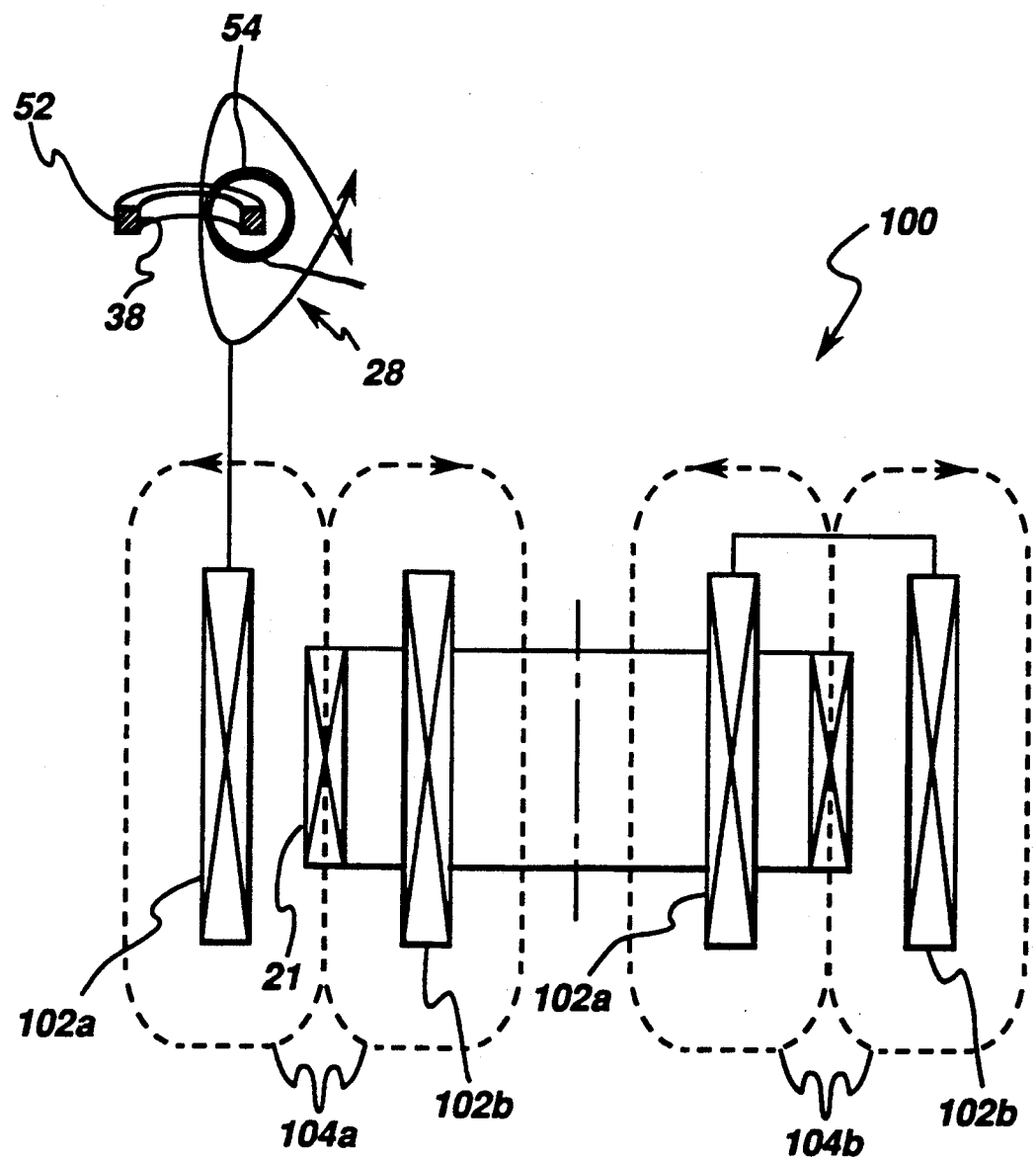
FIG. 6c is a third embodiment of an apparatus for placing a background magnetic field on a bifilar and a loop/switch for the bifilar coil.

With respect to FIGS. 6a–6c, an improvement in the measurement and the information which may be derived therefrom can be realized by operating all or part of the bifilar coil winding 21 in a background magnetic field 104 of background field assembly 100. Since the conductor under test will eventually be wound into a field-producing coil, it will operate in a field. The characteristics of a superconductor vary depending on the field, so it is best to measure the resistance of the test length of conductor in a background field 104 which approximates that in which it will operate. Several alternatives for producing such a field with a solenoidal coil 102 are described here:

1. Place solenoid 102, which is small relative to the bifilar coil, winding 21 against the side flange of the bifilar coil winding 21, thus exposing part of the bifilar coil winding 21 to field 104 (FIG. 6a);
2. Insert the bifilar coil winding 21 in the bore of a large solenoid 102 (FIG. 6b);
3. Insert the bifilar coil winding 21 in the radial gap between two solenoids 102a and 102b which produce fields 104a and 104b, respectively, in the same direction in the gap (FIG. 6c). This option allows a fairly low field 104a and 104b to be generated in the central region of the interior field coil, where very convenient measurements free of background field can be made that include all features of the Hall sensor 38, loop extensions or switch 28 and rings 52.

The stabilizing of the background field coil current can be accomplished by using a commercially available highly stable power supply (available to stability levels of 10 ppm or better) or a superconducting switch. In fact, an acceptable level of insensitivity to field fluctuations can be achieved with a standard power supply (100 ppm or so) because the mutual inductance between the background field solenoid 102 and the bifilar coil 21 is reduced by the ratio of the volume of the bifilar winding to the cylindrical volume enclosed by the bifilar coil 21. This ratio is about 4%, so a 100 ppm stability in the power supply for the background field coil 102 translates into a 4 ppm stability of the bifilar persistent current loop. This value is much better than the resolution of the Hall sensor measuring device and the ferrite coil coupling.

Once given the above disclosure, many other features, modifications and improvements will become apparent to the skilled artisan. Such features, modifications and improvements are, therefore, considered to be part of this invention, the scope of which is to be determined by the following claims.

What is claimed is:

1. An apparatus for measuring the electrical resistance of a superconductor, said apparatus comprised of:
   a plural turn bifilar coil winding of a superconducting material having an electrical switch means in the form of a single turn loop substantially integral with said winding and located at a predetermined distance away from said winding; and
   a magnetic field measuring means located substantially adjacent to said switch means for providing a measurement of the electrical resistance of said winding.

2. The apparatus, according to claim 1, wherein said magnetic field measuring means is further comprised of:
   a ferromagnetic ring means located adjacent said switch means; and
   a calibration winding located on said ring means.

3. The apparatus, according to claim 2, wherein said ring means is further comprised of:
   a gap located on said ring means; and
   a sensor means located adjacent said gap.

4. The apparatus, according to claim 3, wherein said sensor means is further comprised of:
   a Hall sensor.

5. The apparatus, according to claim 1, wherein said magnetic field measuring means is further comprised of:
   a Hall sensor.

6. The apparatus, according to claim 1, wherein said apparatus is further comprised of:
   a magnetic field generating means located adjacent said bifilar coil winding.

7. The apparatus, according to claim 6, wherein said magnetic field generating means is further comprised of:
   a solenoid.

8. A method for measuring the electrical resistance of a superconductor including a bifilar superconducting winding having first and second conductors wound in a plurality of turns in a first direction, an end on said first conductor, an end on said second conductor, said ends being connectable to complete the radially outermost turn of said winding, a mandrel adjacent to said winding and a magnetic field measuring means, wherein said method is comprised of the steps of:
   wrapping a portion of the radially outermost turn of said first conductor around said mandrel in a second direction to provide a switch in the form of a loop which is opposite in direction to said first direction;
   electrically connecting said ends of said first and second conductors;
   inducing a current in said winding to create a resistance in said winding;
   inserting said magnetic field measuring means adjacent said switch; and
   measuring said electrical resistance in said superconductor with said magnetic field measuring means.

9. The method, according to claim 8, wherein said step of inducing a current in said winding is further comprised of the steps of:
   powering a heater located adjacent said loop;
   energizing a power lead means that is electrically connected to said loop; and
   stabilizing said current in said winding.

10. The method, according to claim 8, wherein said method is further comprised of the step of:
    creating a magnetic field adjacent to said winding.

11. The method, according to claim 8, wherein said step of wrapping said first conductor is further comprised of the step of:
    forming said loop such that said loop is in a geometrical plane that is substantially perpendicular to a longitudinal axis of said bifilar winding.

12. The method, according to claim 8, wherein said step of wrapping said first conductor is further comprised of the step of:
    forming said loop such that said loop is in a geometrical plane that is substantially perpendicular to a circumferential direction of said bifilar winding.

* * * * *